US007223269B2

(12) United States Patent
Chappuis

(10) Patent No.: US 7,223,269 B2
(45) Date of Patent: May 29, 2007

(54) FACET FUSION SYSTEM

(76) Inventor: James L. Chappuis, 3170 Lakeridge Dr., Marietta, GA (US) 30067

( * ) Notice: Subject to any disclaimer, the term of this patent is extended or adjusted under 35 U.S.C. 154(b) by 369 days.

(21) Appl. No.: 10/725,832

(22) Filed: Dec. 2, 2003

(65) Prior Publication Data
US 2004/0111093 A1 Jun. 10, 2004

Related U.S. Application Data

(60) Provisional application No. 60/430,311, filed on Dec. 2, 2002.

(51) Int. Cl.
*A61F 5/00* (2006.01)
(52) U.S. Cl. ...................................... 606/86
(58) Field of Classification Search ................ 606/79, 606/80, 86, 90, 96, 102, 104, 61; 623/17.11–17.16
See application file for complete search history.

(56) References Cited
U.S. PATENT DOCUMENTS
6,332,886 B1 * 12/2001 Green et al. ................ 606/80

| 6,565,605 | B2 * | 5/2003 | Goble et al. | 623/17.11 |
| 6,695,851 | B2 * | 2/2004 | Zdeblick et al. | 606/96 |
| 6,921,403 | B2 * | 7/2005 | Cragg et al. | 606/86 |
| 2002/0065558 | A1 * | 5/2002 | Varga et al. | 623/17.11 |
| 2005/0124993 | A1 * | 6/2005 | Chappuis | 606/61 |

* cited by examiner

Primary Examiner—Eduardo C. Robert
Assistant Examiner—Michael J. Araj
(74) Attorney, Agent, or Firm—Thomas, Kayden, Horstemeyer & Risley, LLP

(57) ABSTRACT

A facet fusion system comprises a trochar and a retractor arranged and configured for use during percutaneous retraction. A facet bur is adapted for decorticating the facet joint. The trochar, retractor and facet bur are implemented to prepare the facet joint for fusion. The facet bur comprises a head and a shaft. The head has a planar and an extension extending from the planar. The shaft extends from the planar of the head and extends from the planar in a direction opposing the extension of the head. The shaft is also adapted releasably to engage a power source for rotation. The extension is arranged and configured to engage a facet joint to taper the facet joint. The planar is arranged and configured to engage and plane a posterior surface of the facet.

7 Claims, 7 Drawing Sheets

FACET FUSION SYSTEM

CROSS-REFERENCE TO RELATED APPLICATION

This application claims priority to copending U.S. provisional application entitled, "Facet Fusion Apparatus and Method of Use," having Ser. No. 60/430,311, filed on Dec. 2, 2002, which is entirely incorporated herein by reference.

FIELD OF THE INVENTION

The present invention generally relates to surgical instruments, and in particular, relates to a facet fusion system.

DESCRIPTION OF RELATED ART

Skeletal structures are formed of bones and adjoining structures which include cartilage, for instance. For various reasons, these skeletal structures may require artificial support or stabilization. For example, the human spine is composed of a column of thirty-three bones, called vertebrae, and their adjoining structures. The twenty-four vertebrae nearest the head are separate bones capable of individual movement and generally are connected by anterior and posterior longitudinal ligaments and by discs of fibrocartilage, called intervertbral discs, positioned between opposing faces of adjacent vertebrae. Each of these vertebrae include a vertebral body and a dorsal arch that enclose an opening, called the vertebral foramen, through which the spinal cord and spinal nerves pass. The remaining nine vertebrae are fused to form the sacrum and the coccyx and are incapable of individual movement.

Each vertebra capable of individual movement is joined to the adjoining vertebra at facet joints. Facet joints allow for movement of the spine in all directions. Arthritis, degenerative disc disease and other various degenerative conditions can result in the need to fuse the facet joints together.

Facet joint fusion can reduce or eliminate pain and/or complications experienced by patients with degenerating facet joints. Currently, facet joints are fused by decorticating the joint in an open procedure followed by packing in bone implant. In this process, often times the facet joint is not completely decorticated resulting in a low fusion success rate.

Thus, a heretofore unaddressed need exists in the industry to address the aforementioned deficiencies and inadequacies.

SUMMARY OF THE INVENTION

Preferred embodiments of the present invention provide a facet fusion system for fusing a facet joint. Briefly described in architecture, one embodiment of the system can be implemented as follows. A facet fusion system comprises a trochar and a retractor, both being arranged and configured for use during percutaneous retraction. A facet bur is adapted for decorticating the facet joint. The trochar, retractor and facet bur are implemented to prepare the facet joint for fusion.

Other systems, methods, features and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE SEVERAL VIEWS OF THE DRAWINGS

The invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DESCRIPTION OF THE PREFERRED EMBODIMENTS

Referring to FIGS. 1 through 6, an embodiment of elements of the facet fusion system of the present invention is illustrated. First, with reference to FIGS. 1 and 2, a trochar 10 and retractor 20 are illustrated, respectively. The trochar 10 comprises a hollow body portion having at least one tapered end. The trochar 10 preferably includes a substantially sharpened, pointed tip toward the tapered end. The retractor 20 comprises a main body portion 22 having a handle 24 extending therefrom. The main body portion 22 is preferably hollow. The trochar 10 and the retractor 20 are used to perform percutaneous retraction and dissection of the facet joint in a manner known to those skilled in the art. More specifically, the trochar 10 is placed into a position such as to dilate surrounding muscle. The retractor 20 is then placed over the facet joint. The retraction and dissection partially prepares the facet joint for fusion.

Figure 1:
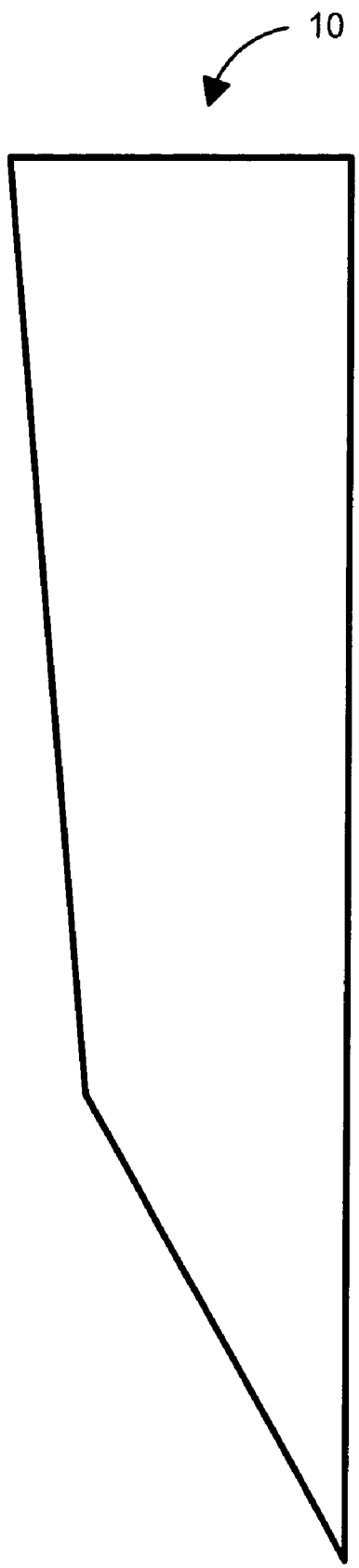
FIG. 1 illustrates a view of an embodiment of a trochar of the present invention.
Figure 2:
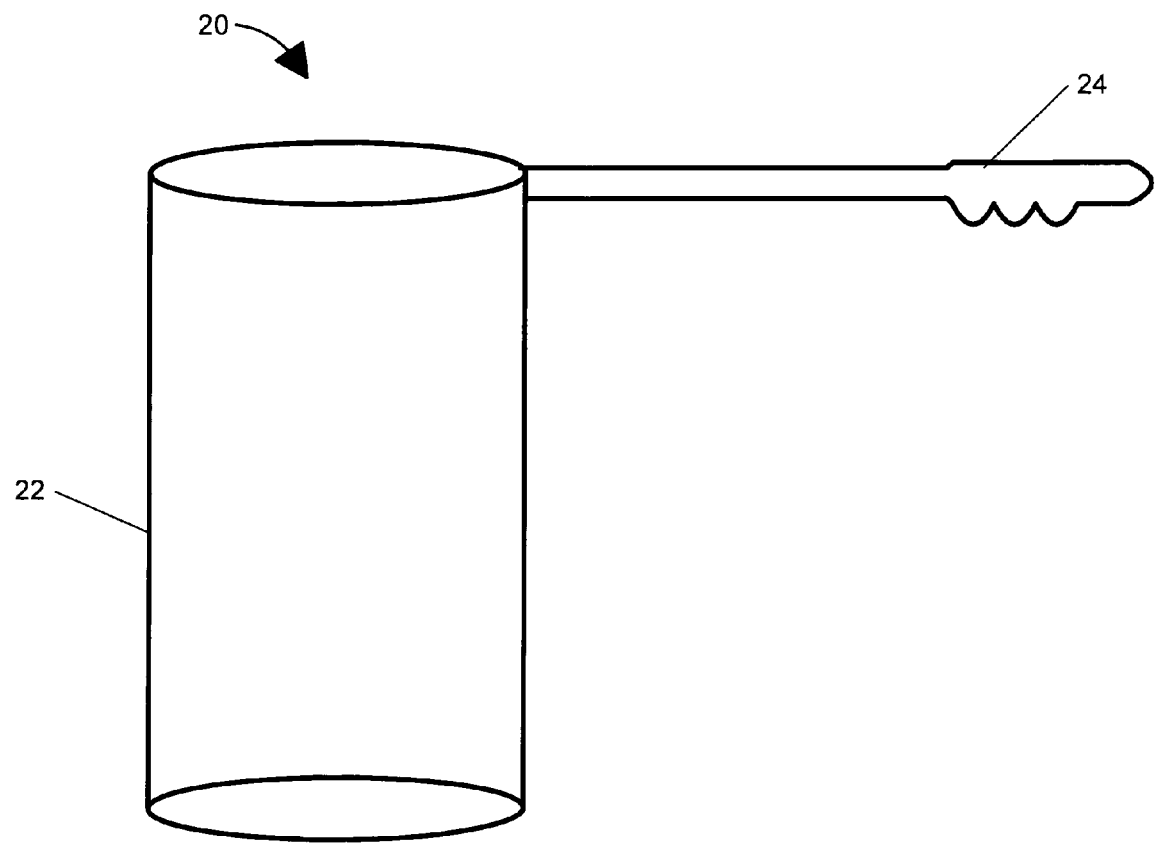
FIG. 2 illustrates a view of an embodiment of a retractor of the present invention.
Figure 3:
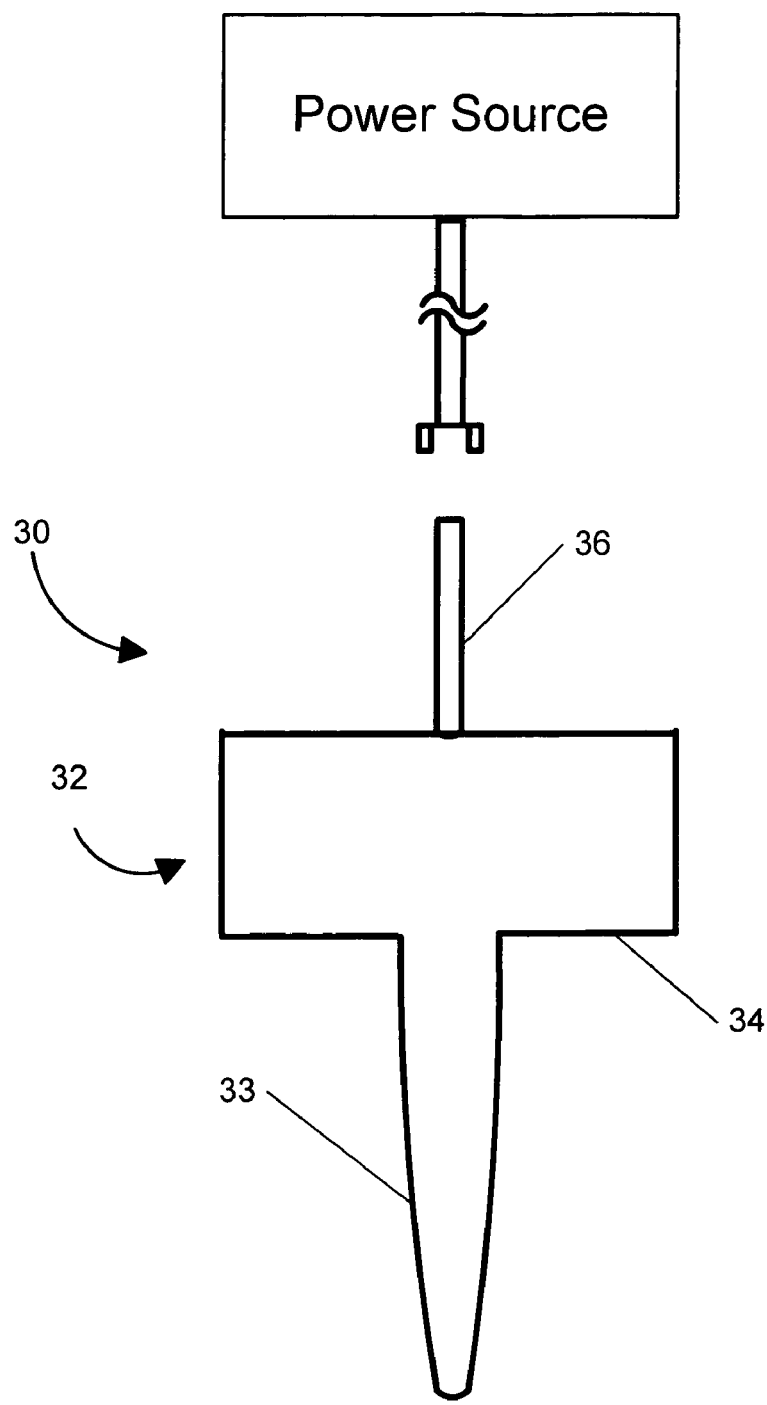
FIG. 3 illustrates a view of an embodiment of a facet bur and planer of the present invention.

Referring next to FIG. 3, a facet bur 30 of the system is illustrated. The facet bur 30 comprises a head 32 having a substantially T-shaped cross-section. The head 32 comprises an extension 33 and a planar 34. The bur 30 includes a shaft 36 extending from the head 32. The shaft 36 is adapted releasably engage a power source for rotation, such as a surgical drill, or the like. The head 32 is arranged and configured to decorticate the facet joint upon being engaged therewith while rotating at a desired speed, thereby tapering the facet joint into a substantially wedge shaped configuration. While tapering the facet joint with the extension 33, the planar 34 disposed substantially adjacent the extension 33, engages a posterior surface of the facet in order to plane the surface thereof. The extent to which the top of the facet is planed is determined by the configuration of implant 50 to be used. Implementation of an implant 50 with a planar portion cap 58 requires a greater degree of planing to the facet.

Figure 4:
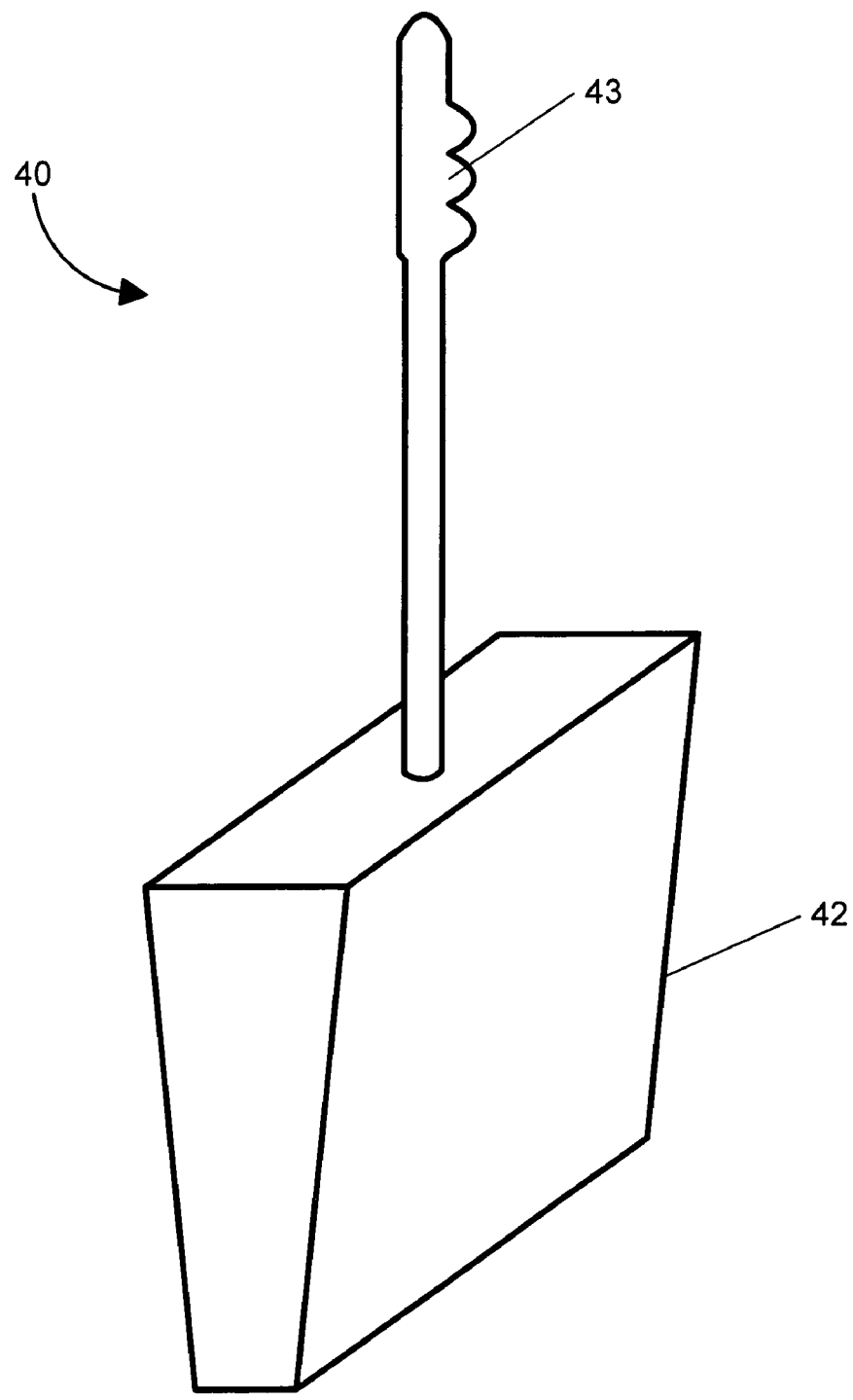
FIG. 4 illustrates a view of an embodiment of a facet sizer of the present invention.

FIG. 4 illustrates a facet sizer 40 of the system. It should be noted that the system preferably comprises a plurality of facet sizers 40, each having at least a slight dimension variation. Each facet sizer 40 comprises a body portion 42 and a handle 43. It should be understood that although the body portion 42 is illustrated as being substantially wedge-shaped, it can comprise any suitable configuration. After the facet to be fused has been located, decorticated and planed as desired and described herein, the facet sizer 40 is inserted into the area of the facet joint where an implant 50 will be positioned in order to fuse the facet. Facet sizers 40 of various dimensions can be placed in the facet one after the other until the user can ascertain the necessary implant size to be placed in the facet for fusion.

Figure 5:
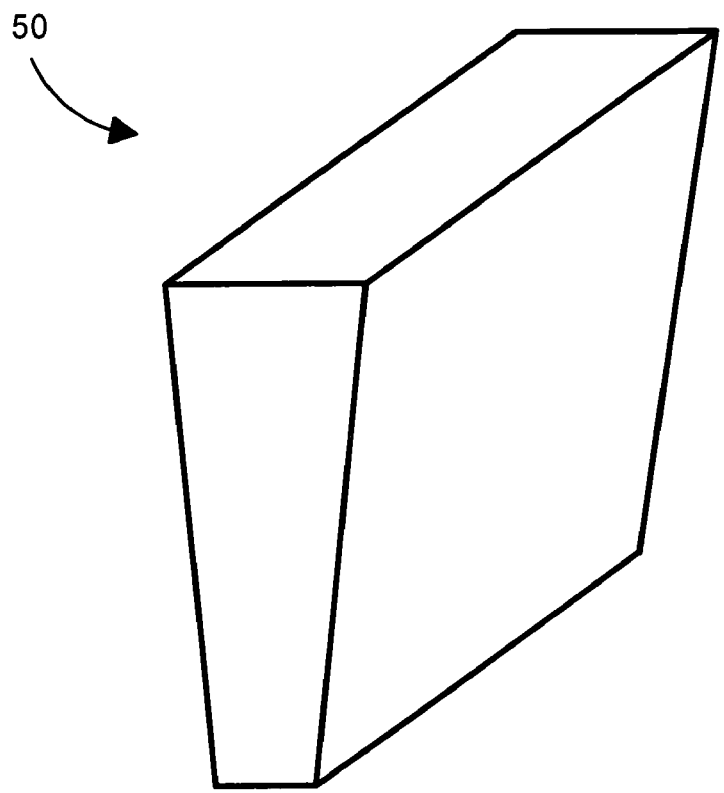
FIG. 5 illustrates a view of an embodiment of an implant of the present invention.

A graft or implant 50, such as illustrated in FIG. 5, is positioned in the facet joint for fusion. The implant 50 selected preferably substantially corresponds in dimension to the facet sizer 40 that the user determined was the appropriate size for the fusion. The burring of the facet and wedging of the implant 50 into position results in a sufficient amount of friction to hold the implant 50 in the desired position. The implant 50 can comprise, bone, coral, or any suitable material lending itself to fusion in such an environment. The implant 50 is illustrated as comprising a tapered shape, however, it should be understood that the implant 50 can comprise any suitable configuration.

Figure 5A:
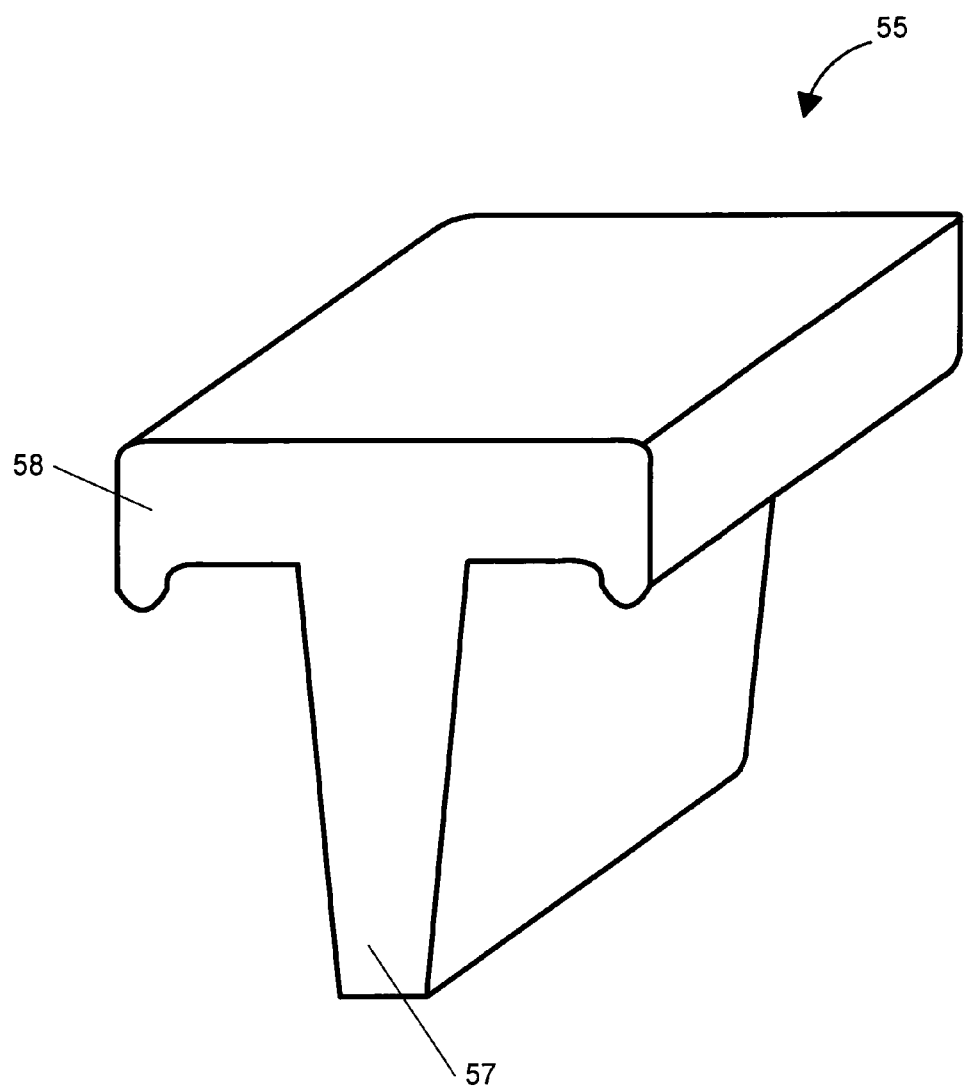
FIG. 5A illustrates a view of an embodiment of an implant of the present invention.

FIG. 5A illustrates an embodiment of a synthetic implant 55 that may be implemented in the facet fusion system. The synthetic implant 55 comprises a fusion portion 57 and a cap 58. The fusion portion 57 is adapted to engage an internal portion of the facet joint. The cap 58 is adapted to engage a posterior portion of the facet joint in order to secure to implant 55 in the desired position. The fusion portion 57 is illustrated as having a tapered cross-section; however, it should be understood that the fusion portion 57 can comprise any suitable configuration. The synthetic implant 55 comprises a polished stainless steel, high-density polyethylene, or any suitable material. Similar to implant 50, implant 55 is selected in a size and configuration substantially corresponding to that indicated as appropriate by the facet sizer 40. The burring of the facet and wedging of an appropriately sized and configured implant 55 into position results in a sufficient amount of friction to hold the implant 55 in the desired position.

Figure 6:
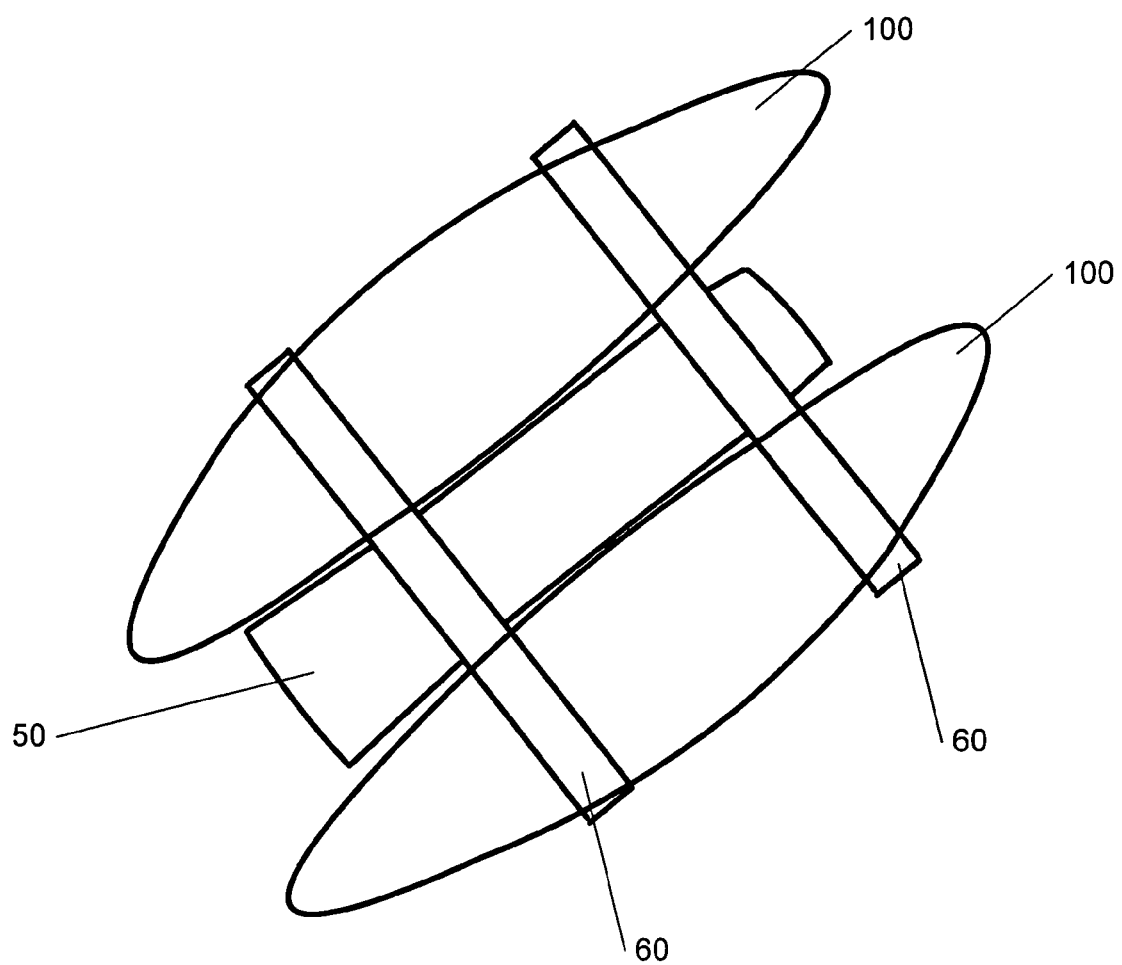
FIG. 6 illustrates a view of an embodiment of a staple of the present invention.

FIG. 6 illustrates an optional stapling device 60. The stapling device 60 can be implemented after the appropriate size implant 50, 55 is selected and positioned on the facet joint 100 such that the device 60 engages the facet joint 100 and the implant 50, 55. The stapling device 60 secures the implant 50, 55 in position in the facet joint 100. The stapling device 60 comprises any suitable material that can be heated to allow for some compression, such as Nitinol, or the like.

It should be emphasized that the above-described embodiments of the present invention, particularly, a "preferred" embodiment, are merely possible examples of implementations, merely set forth for a clear understanding of the principles of the invention. Many variations and modification may be made to the above-described embodiment(s) of the invention without departing substantially from the spirit and principles of the invention. All such modifications and variations are intended to be included herein within the scope of this disclosure and the present invention and protected by the following claims.

Therefore, having thus described the invention, at least the following in claimed:

1. A facet fusion system for fusing a facet joint comprising:
   a trochar arranged and configured for use during percutaneous retraction;
   a retractor arranged and configured for use during percutaneous retraction; and
   a facet bur arranged and configured for decorticating the facet joint, said facet bur comprising:
   a shaft being adapted releasably to engage a power source for rotation; and
   a head having a planar and an extension extending from said planar;
   wherein said planar extends laterally outward from a longitudinal axis of said head;
   wherein said shaft extends from said planar of said head and extends from said planar in a direction opposing said extension of said head;
   wherein said extension is tapered to engage a facet joint to taper said facet joint and said planar has an abrasive surface to engage and plane a posterior surface of the facet joint while the extension is inserted into the facet joint;
   wherein said trochar, said retractor, and said facet bur are implemented to prepare the facet joint for fusion.

2. The facet fusion system of claim 1, further comprising:
   a facet sizer arranged and configured to aid in the determination of an appropriate size implant to be inserted into the facet joint to facilitate fusion.

3. A facet fusion system of claim 1, further comprising:
   an implant arranged and configured to facilitate fusion of the facet joint.

4. A facet fusion system of claim 3, further comprising:
   staple means for fixing said implant in position in the facet joint;
   wherein said staple means facilitates fusion of the facet joint with said implant.

5. A facet fusion system for fusing a facet joint comprising:
   a trochar arranged and configured for use during percutaneous retraction;
   a retractor arranged and configured for use during percutaneous retraction; and
   a facet bur arranged and configured for decorticating the facet joint, said facet bur comprising:
   a shaft being adapted releasably to engage a power source for rotation; and
   a head having a planar and an extension extending from said planar;
   wherein said planar extends laterally outward from a longitudinal axis of said head;

wherein said shaft extends from said planar of said head and extends from said planar in a direction opposing said extension of said head;

wherein said extension is tapered to engage a facet joint to taper said facet joint and said planar has an abrasive surface to engage and plane a posterior surface of the facet joint while the extension is inserted into the facet joint;

wherein said trochar, said retractor, and said facet bur are implemented to prepare the facet joint for fusion;

a facet sizer arranged and configured to aid in the determination of an appropriate size implant to be inserted into the facet joint to facilitate fusion comprising:

a body portion; and a handle extending from said body portion;

wherein said body portion is arranged and configured to aid in the determination of an appropriate size implant to be inserted into the facet joint to facilitate fusion.

6. A facet fusion system of claim 5, further comprising:

an implant arranged and configured to facilitate fusion of the facet joint.

7. A facet fusion system of claim 6, further comprising:

staple means for fixing said implant in position in the facet joint;

wherein said staple means facilitates fusion of the facet joint with said implant.

* * * * *